United States Patent
Baldauf et al.

(10) Patent No.: US 11,626,208 B2
(45) Date of Patent: Apr. 11, 2023

(54) SYSTEM, METHOD AND COMPUTER PROGRAM PRODUCT FOR ENSEMBLE-BASED COGNITIVE ONLINE HEALTH SYSTEM FOR EFFECTIVE DISEASE DIAGNOSIS

(71) Applicant: International Business Machines Corporation, Armonk, NY (US)

(72) Inventors: Julia Baldauf, Southgate (AU); Lida Ghahremanlou, Southgate (AU); Fatemeh Jalali, Hawthorn East (AU); Mahsa Salehi, Southgate (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 570 days.

(21) Appl. No.: 15/252,525

(22) Filed: Aug. 31, 2016

(65) Prior Publication Data

US 2018/0060510 A1 Mar. 1, 2018

(51) Int. Cl.
*G16H 50/20* (2018.01)
*G16H 80/00* (2018.01)

(52) U.S. Cl.
CPC ............. *G16H 50/20* (2018.01); *G16H 80/00* (2018.01); *Y02A 90/10* (2018.01)

(58) Field of Classification Search
CPC ........ G16H 50/20; G16H 80/00; Y02A 90/26; Y02A 90/10
See application file for complete search history.

(56) References Cited

U.S. PATENT DOCUMENTS

| | | | | |
|---|---|---|---|---|
| 9,424,532 | B1* | 8/2016 | Abedini | G06N 20/00 |
| 2007/0282637 | A1* | 12/2007 | Smith | G16H 10/60 |
| | | | | 705/3 |
| 2009/0083075 | A1* | 3/2009 | Henschke | G16H 50/20 |
| | | | | 705/3 |
| 2009/0259488 | A1* | 10/2009 | Gounares | G16H 70/20 |
| | | | | 705/7.42 |
| 2009/0319291 | A1* | 12/2009 | Noordvyk | G16H 30/40 |
| | | | | 705/2 |
| 2014/0100882 | A1* | 4/2014 | Hamilton | G16H 50/70 |
| | | | | 705/3 |

(Continued)

OTHER PUBLICATIONS

L. Schindelheim, Gina & A. Jerrard, David & Witting, Michael. Patient Preference for Emergency Physician Age and Gender, Oct. 2004, The American Journal of Emergency Medicine, vol. 22, p. 503. Retrieved from: https://www.sciencedirect.com/science/article/pii/S0735675704001810?via%3Dihub (Year: 2004).*

(Continued)

*Primary Examiner* — Sheetal R Paulson
(74) *Attorney, Agent, or Firm* — Joseph Petrokaitis, Esq.; McGinn I.P. Law Group, PLLC.

(57) ABSTRACT

A diagnosis method, system, and computer program product, include processing a user input comprising medical symptoms, assigning the user to a team of physicians and a cognitive agent based on the processed medical symptoms, each of the physicians having a different medical specialty corresponding to a disease associated with the medical symptoms, and producing a consensus diagnosis from the team of physicians and the cognitive agent.

8 Claims, 11 Drawing Sheets

(56) References Cited

U.S. PATENT DOCUMENTS

| | | | | |
|---|---|---|---|---|
| 2014/0324450 A1* | 10/2014 | Hicks | G16H 40/20 | 705/2 |
| 2015/0073824 A1* | 3/2015 | Norris | G06F 16/24575 | 705/2 |
| 2015/0248536 A1* | 9/2015 | Tawil | G16H 30/20 | 705/3 |
| 2016/0012194 A1* | 1/2016 | Prakash | G16H 40/40 | 705/2 |
| 2016/0357936 A1* | 12/2016 | Ghouri | G16H 50/70 | |
| 2017/0039324 A1* | 2/2017 | Francois | G16H 50/30 | |

OTHER PUBLICATIONS

Nolen, H. A., Moore, J. X., Rodgers, J. B., Wang, H. E., & Walter, L. A. Jun. 27, 2016. Patient Preference for Physician Gender in the Emergency Department.;The Yale journal of biology and medicine;89(2), 131-42. Retrieved from: https://www.ncbi.nlm.nih.gov/pmc/articles/PMC4918861/ (Year: 2016).*

F.Porter, James et.al Feb. 1988. The AI-RHEUM knowledge-based computer consultant system in rheumatology performance in the diagnosis of 59 connective tissue disease patients from Japan. 31. 219-26. Retrieved from: https://onlinelibrary.wiley.com/doi/abs/10.1002/art.1780310210?sid=nlm%3Apubmed (Year: 1988).*

M. McDonald, Kathryn & L. Bryce, Cindy & L. Graber, Mark. The patient is in: patient involvement strategies for diagnostic error mitigation. Jul. 26, 2013, BMJ Quality and Safety, 22:ii33-ii39. Retrieved from: https://qualitysafety.bmj.com/content/22/Suppl_2/ii33 (Year: 2013).*

Zhou, X.Z. et al. Human symptoms-disease network. Jun. 26, 2014 Nat. Commun. 5:4212. Retrieved from: https://www.nature.com/articles/ncomms5212 (Year: 2014).*

Zhou, Menche, Barabasi, Sharma, Human symptoms-disease network, Jun. 26, 2014, Nature communications (Year: 2014).*

McDonald, Bryce, Graber, The patient is in: patient involvement strategies for diagnostic error mitigation, BMJ Qual Saf 2013; 22 ii33-ii39. (Year: 2013).*

Mel, et al. "The NIST Definition of Cloud Computing". Recommendations of the National Institute of Standards and Technology. Nov. 16, 2015.

* cited by examiner

DIAGNOSIS METHOD 100

FIG. 5A

SYSTEM, METHOD AND COMPUTER PROGRAM PRODUCT FOR ENSEMBLE-BASED COGNITIVE ONLINE HEALTH SYSTEM FOR EFFECTIVE DISEASE DIAGNOSIS

BACKGROUND

The present invention relates generally to a diagnosis method, and more particularly, but not by way of limitation, to a system, method, and computer program product for a disease diagnosing method with the use of diverse physicians and cognitive intelligent agents.

Conventionally, patients often complain about the lack of precise diagnosis of their medical problems as well as the lengthy process of finding a matched specialist for their disease who can correctly diagnose the patient. In particular, diagnosis of some diseases with common symptoms is very difficult, and often requires a team of specialists. For example, symptoms can be related to a multitude of diseases and different specialty doctors may interpret the symptoms differently. This can lead to an increase in health care cost as well as an inefficiency in the conventional diagnosing techniques.

Conventional techniques consider communication between a patient and a corresponding physician without making physical appointments via an online system. However, these types of techniques may only allow a patient and doctor to connect more easily but does not improve the accuracy of the diagnosis of the patient.

Other conventional techniques consider facilitating interaction with multiple doctors and a patient by supporting several physicians located at a different place and time to access the system at a designated time to conduct a medical treatment and a medical consultation service by a team of medical professionals has been considered that can provide information as to the sum of the opinions of medical professions.

However, there is a technical problem in the conventional techniques in that the conventional techniques do not consider the notion of diversity amongst specialties of doctors in selecting and matching medical professions. Moreover, the conventional techniques do not take advantage of a feedback module and cognitive agents. For example, the conventional techniques cannot solve a need in the art for a plurality of different specialty doctors (e.g., muscular, neuro, gastro, etc.) to assess the symptoms which may be commonly linked to diseases within the specialty. That is, the conventional techniques consider an entirely different approach to diagnosing patients that leads to an inefficient and inaccurate diagnosis.

SUMMARY

In an exemplary embodiment, the present invention can provide a computer-implemented diagnosis method, the method including processing a user input comprising medical symptoms, assigning the user to a team of physicians and a cognitive agent based on the processed medical symptoms, each of the physicians having a different medical specialty corresponding to a disease associated with the medical symptoms, and producing a consensus diagnosis from the team of physicians and the cognitive agent.

One or more other exemplary embodiments include a computer program product and a system.

Other details and embodiments of the invention will be described below, so that the present contribution to the art can be better appreciated. Nonetheless, the invention is not limited in its application to such details, phraseology, terminology, illustrations and/or arrangements set forth in the description or shown in the drawings. Rather, the invention is capable of embodiments in addition to those described and of being practiced and carried out in various ways and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

Aspects of the invention will be better understood from the following detailed description of the exemplary embodiments of the invention with reference to the drawings, in which:

FIG. 5A-5E exemplarily depicts a Graphical User Interface (GUI) embodying the method 100;

DETAILED DESCRIPTION

Figure 1:
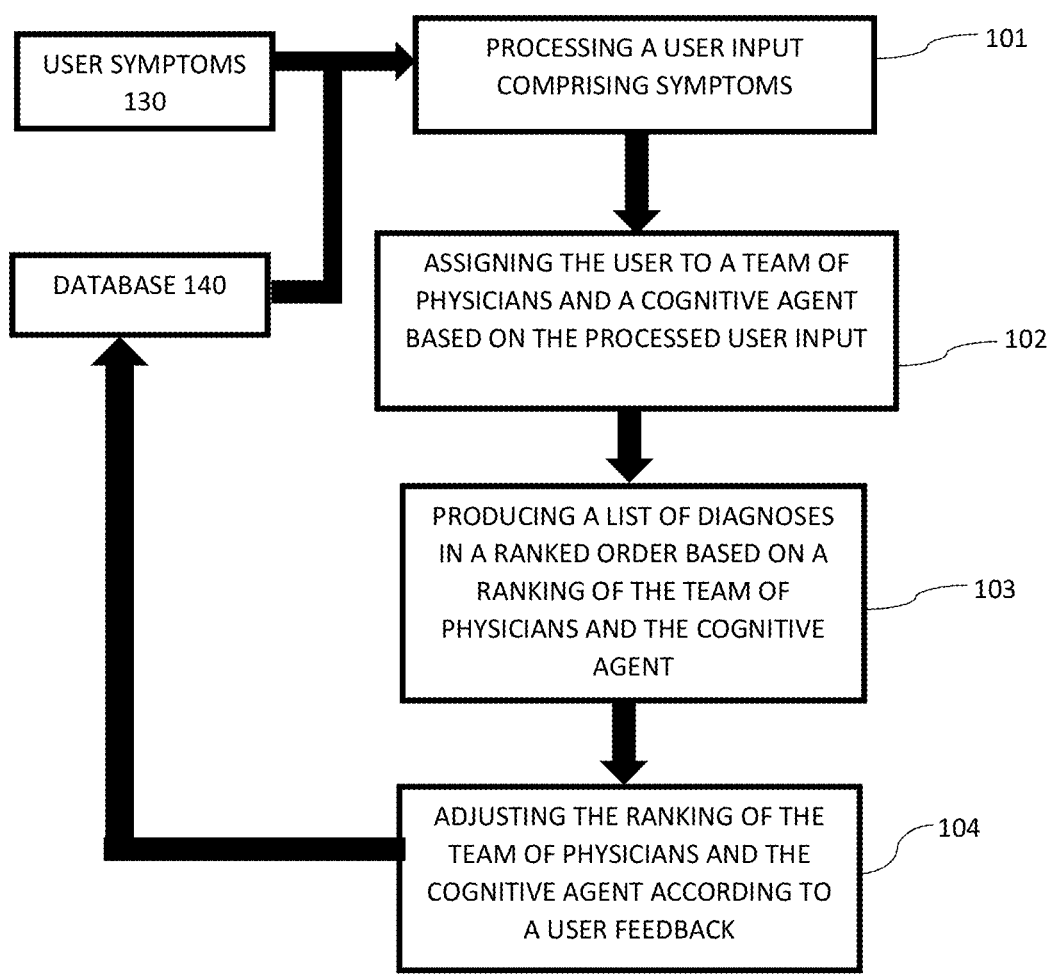
FIG. 1 depicts a flow chart for a diagnosis method 100 according to an embodiment of the present invention.

The invention will now be described with reference to FIG. 1-8, in which like reference numerals refer to like parts throughout. It is emphasized that, according to common practice, the various features of the drawing are not necessarily to scale. On the contrary, the dimensions of the various features can be arbitrarily expanded or reduced for clarity.

With reference now to the example depicted in FIG. 1, the diagnosis method 100 includes various steps to diagnosis a patient with a disease according to the patient's symptoms by at least proposing an expertise match method using clustering techniques, inducing diversity by considering common symptoms with other diseases and other factors to improve the final decision, introducing a cognitive intelligent agent(s) based on machine learning classifiers, which can be replaced by the physicians, and including a feedback loop, which provides a platform for getting feedback from patients and rank the physicians based on the accuracy of their diagnosis and results. As shown in at least FIG. 6, one or more computers of a computer system 12 according to an embodiment of the present invention can include a memory 28 having instructions stored in a storage system to perform the steps of FIG. 1.

Thus, the diagnosis method 100 according to an embodiment of the present invention may act in a more sophisticated, useful and cognitive manner, giving the impression of cognitive mental abilities and processes related to knowledge, attention, memory, judgment and evaluation, reasoning, and advanced computation. A system can be said to be "cognitive" if it possesses macro-scale properties—perception, goal-oriented behavior, learning/memory and action—that characterize systems (i.e., humans) generally recognized as cognitive.

Although one or more embodiments (see e.g., FIGS. 6-8) may be implemented in a cloud environment 50 (see e.g., FIG. 7), it is nonetheless understood that the present invention can be implemented outside of the cloud environment.

In step 101, user symptoms 130 are received and processed. In some embodiments, a user may so called "log-in" to a system or execute the method 100 in which the user inputs a user input comprising symptoms. It is noted that the patient may express their symptoms based on their understating of their medical problem in nonprofessional (i.e., layman) terms and words. In step 101, the user's symptoms are processed by converting general (layman) terms used for symptoms into medical terms using the Watson Concept Expansion service (or the like).

In step 102, the user is assigned to a team of physicians comprising physicians for each specialty that a symptom may be linked to a disease in (as described later) and a cognitive agent.

Figure 2:
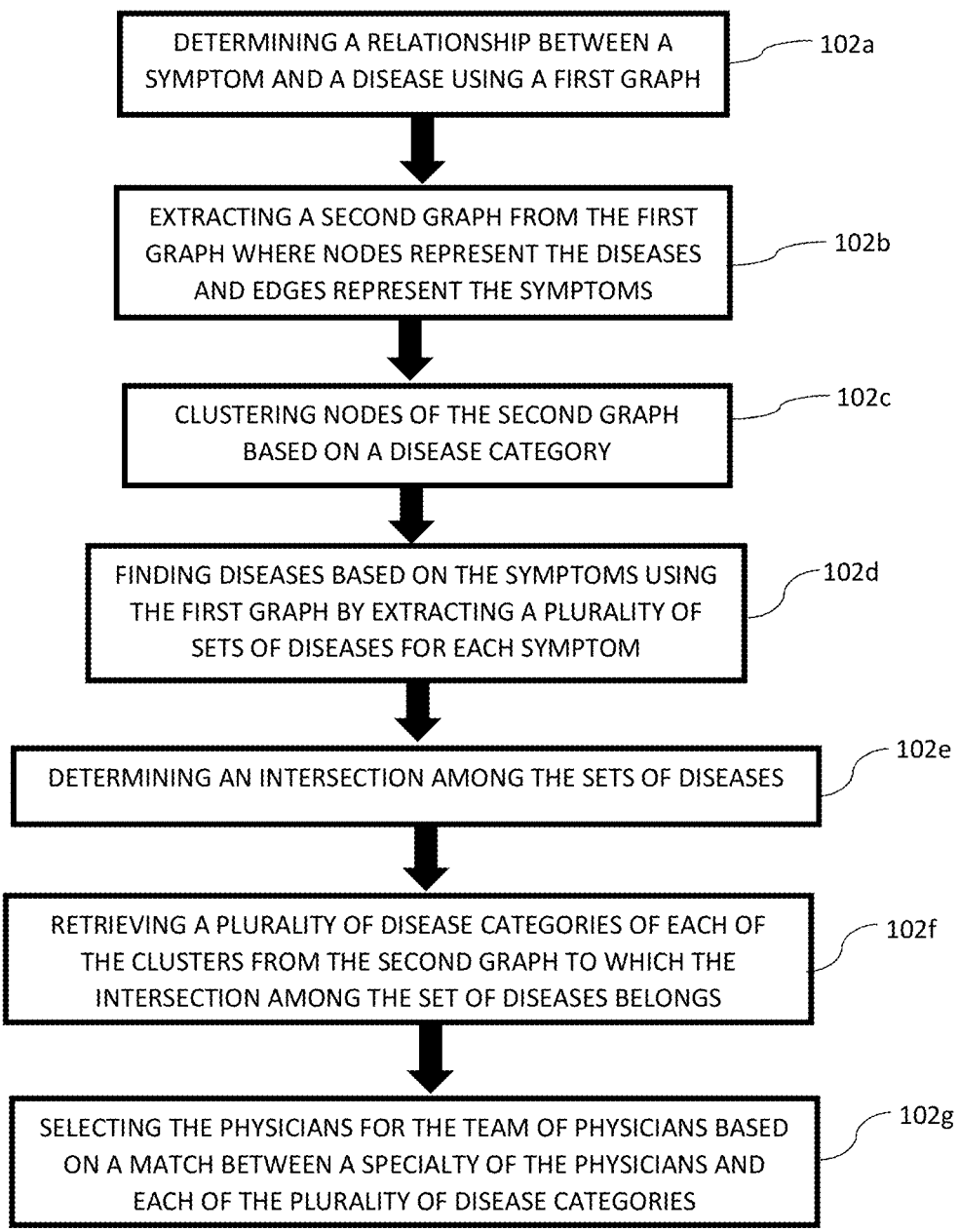
FIG. 2 exemplarily shows a high-level flow chart for an exemplary implementation of step 102 of the diagnosis method 100.

With reference now to FIG. 2, an exemplary implementation of the user being assigned to a team of physicians and a cognitive agent is described according to one embodiment.

Figure 3:
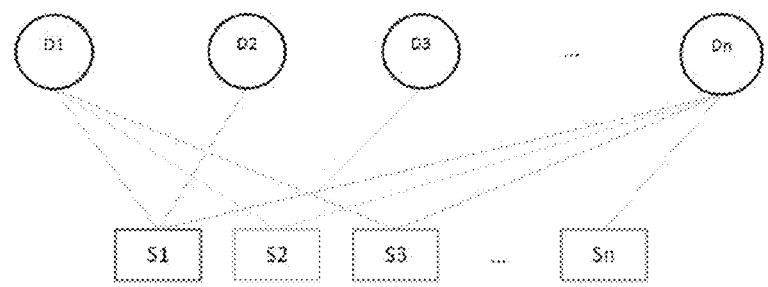
FIG. 3 exemplarily depicts a first graph as a bipartite graph of diseases and symptoms relationships.

In step 102a, a relationship between a symptom and a disease is determined using a first graph as exemplarily shown in FIG. 3. FIG. 3 depicts a bipartite graph of diseases (D)/symptoms (S) relationships. That is, in some embodiments, the first graph comprises the bipartite graph, which indicates the relationship between symptoms and diseases. Each symptom is connected to one or more diseases and each disease is connected to one or more symptoms. The first graph can be retrieved from medical scientific repositories or from past data of the method 100. For example, the first graph can map the relationships between a single symptom and multiple different diseases (e.g., weight gain can be a symptom of depression, pregnancy, etc. headaches may be symptoms of brain tumor, malaria, dehydrations, etc.).

In step 102b, a second graph is extracted from the first graph where nodes of the second graph represent the diseases of the first graph and the edges of the second graph represent the symptoms. As exemplarily shown in FIG. 4, the second graph maps diseases with similar symptoms as strongly connected, whereas diseases that have different symptoms are loosely connected. Hence, the nodes and edges can be clusters (as described later) in the second graph where each cluster represents a disease category corresponding to a type of specialty of a physician.

Figure 4:
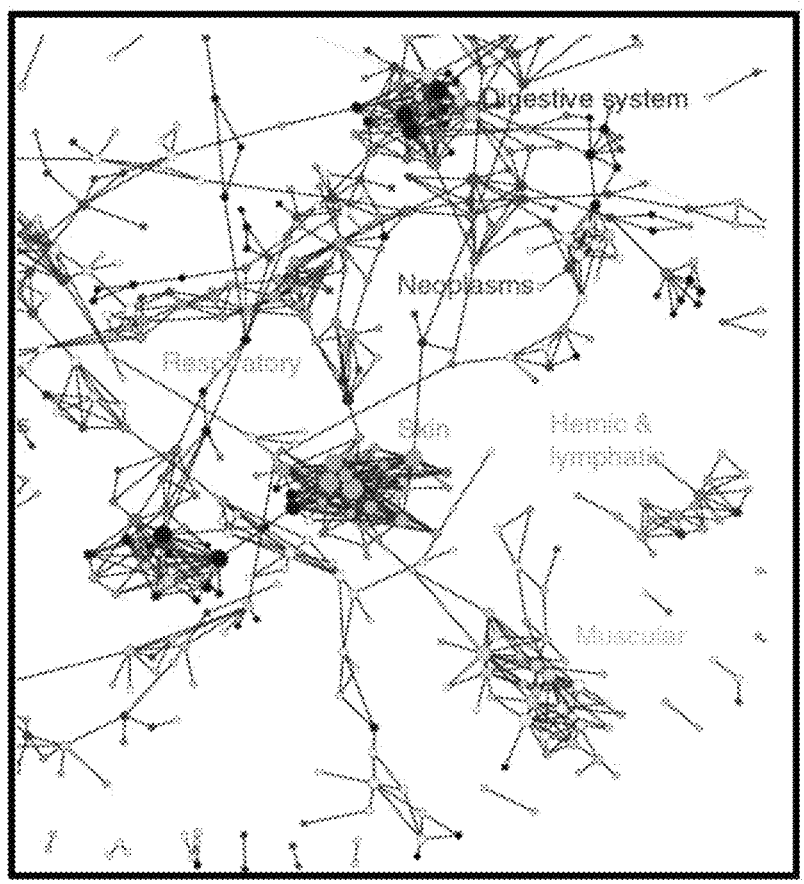
FIG. 4 exemplarily depicts a second graph clustering symptoms with diseases into a specialty type based on the first graph.

In step 102c, the nodes of the second graph are clustered based on the disease category of the nodes. Disease categories that are clustered may include, for example, diseases relating to the digestive system, neoplasms, hemic and lymphatic, skin, respiratory, muscular, etc. For each disease category, the symptoms for the diseases in that category are clustered as shown in FIG. 4.

In step 102d, diseases are found based on the patient symptoms using the first graph. In particular, for each symptom a set of diseases is extracted associated with the symptom. In other words, a set of diseases are selected that have symptoms in common (each disease may have some other symptoms that are not expressed). A probability is given to each disease based on the symptoms that are expressed by the patient. The more that symptoms exist in common, the higher is the probability values of the disease. The top-N (with N being an integer) diseases with high probability values are then selected for specialty selection.

In step 102e, an intersection among all of these sets of diseases is determined as $G_d$.

In step 102f, a plurality of disease categories are retrieved for each of the clusters from the second graph to which the intersection among the set of diseases belongs. That is, the second graph is used to retrieve the clusters to which the diseases in $G_d$ belong (e.g., diseases in the skin cluster, hemic and lymphatic cluster, etc.). Each retrieved cluster refers to a specific disease category. By this technique, the diversity of disease categories relevant to the patient's symptoms may be selected.

In step 102g, physicians for the team of physicians are selected based on a match between a specialty of the physician and each of the plurality of disease categories. For example, a list of disease categories matched with the patient's symptoms is named L. In order to assign the patient's query to a group of physicians related to L, a database 140 of physicians is used along with their specialists, availabilities and rankings.

For example, if the set of diseases includes a disease in the cluster for skin, the category of skin diseases as well as the categories of neoplasms, respiratory, and muscular are retrieved because they intersect with the skin cluster in FIG. 4. Thereby, in step 102g, a plurality of physicians specializing in each of skin, neoplasms, respiratory, and muscular are selected (e.g., a skin physician, a neoplasm physician, a respiratory physicians, and muscular physician). It is noted that since the hemic and lymphatic cluster of diseases in FIG. 4 does not include an intersection with the skin cluster, a physician specializing in hemic and lymphatic medicine is not retrieved.

In some embodiments, the database 140 including the physicians is further arranged based on age, gender and geo-location further to diversify the selected physicians. User preferences can be used to refine the physicians selected in step 102 (102g). For example, a male patient may wish only to be examined by a male doctor or a patient in a particular location may wish to only be examined by a doctor within a predetermined distance of the location.

In step 103, a list of diagnoses is produced in a ranked order based on a ranking of the team of physicians and the cognitive agent. In other words, a consensus of diagnoses is produced based on physicians and/or agents rankings and the final diagnostic decision will be sent to the patient. The list of diseases can be ranked according to past accuracy of the doctors or can be ranked based on a consensus view of the team of physicians. For example, the diagnoses by the skin doctor can be presented first on the list as the most likely disease based on the team of selected physicians agreeing that the skin disease is most likely.

In some embodiments, the ranked list can be ranked based only on the past accuracy of the physicians. That is, in step 104, the rankings of the physicians or agent (or a so called "physician accuracy score") can be adjusted based on a feedback from the user. For example, a patient can provide feedback and rank the physicians based on the accuracy of their diagnostic decision. This will be used for improving the reliability of the diagnoses. That is, if a particular physician's diagnoses is not accurate and costs the patient time and money, the patient can provide feedback to lower the physicians ranking such that other user's can benefit from the knowledge of the patient.

In some embodiments, as the symptoms are processed in step 101, the patient can be iteratively asked questions about other symptoms in more details by using natural language search on databases like PubMed. In addition, after the appropriate specialists are selected, they can also ask for more interactive questions to describe the symptoms to better provide the specialists with needed information. For example, if the symptom is "headache", a specialist could query the user to ask "what part of your head hurts" to determine if the pain is located in the patients eyes, temple, etc.

Figure 5A:
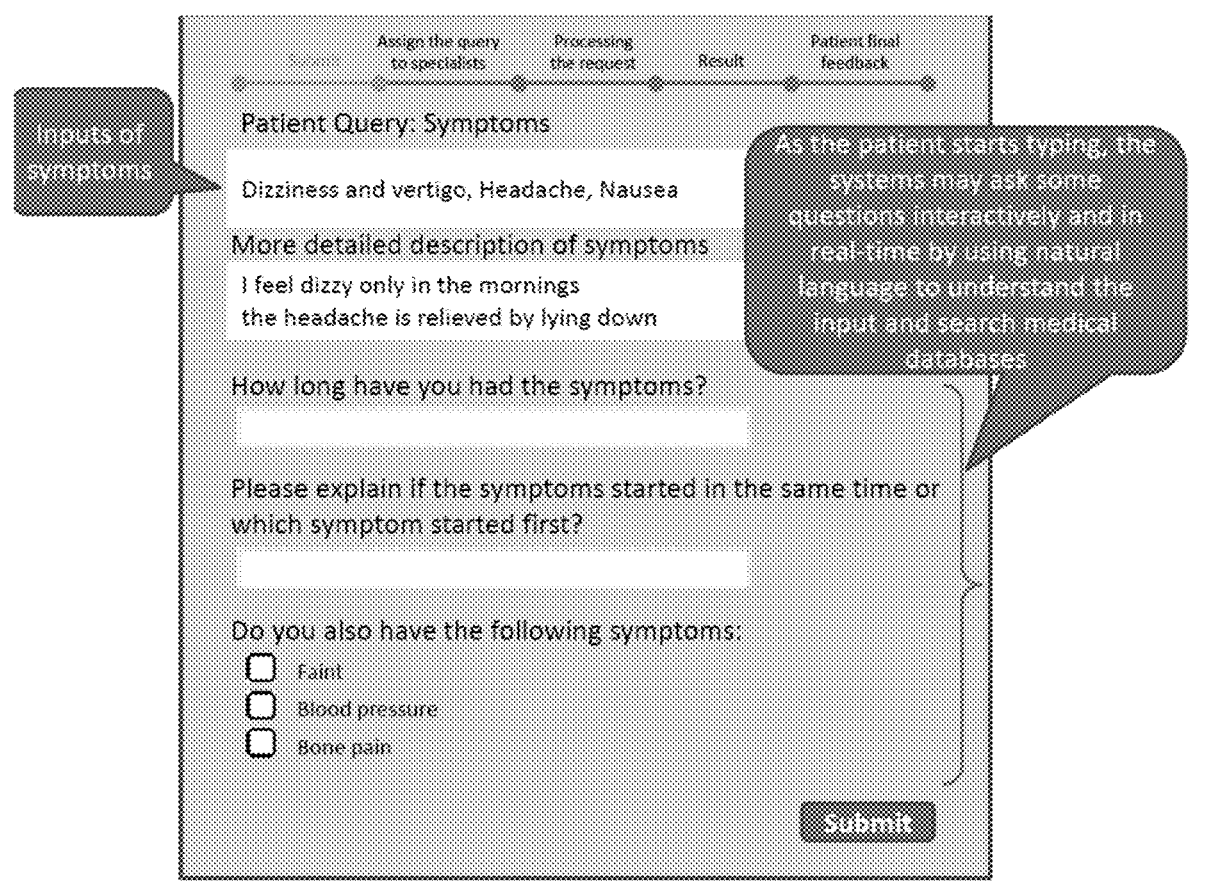
Figure 5B:
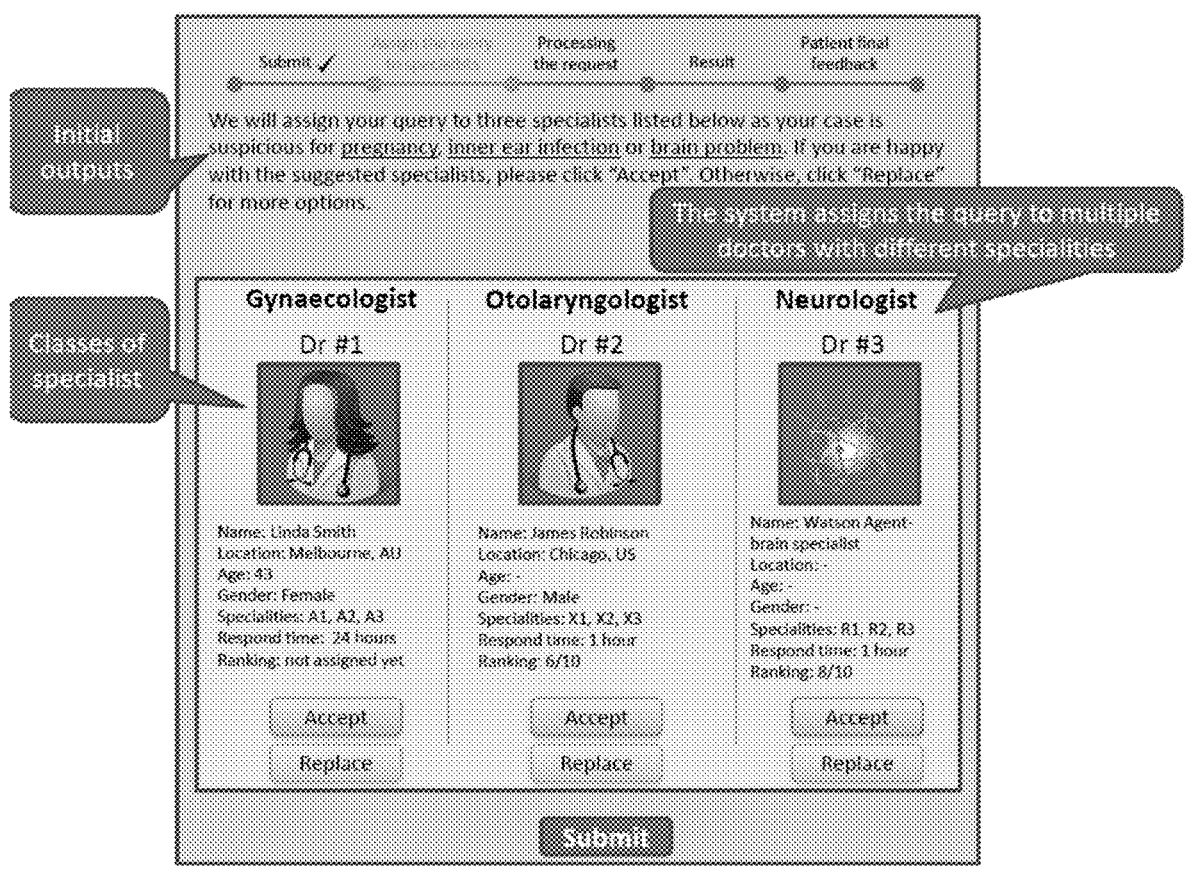
Figure 5C:
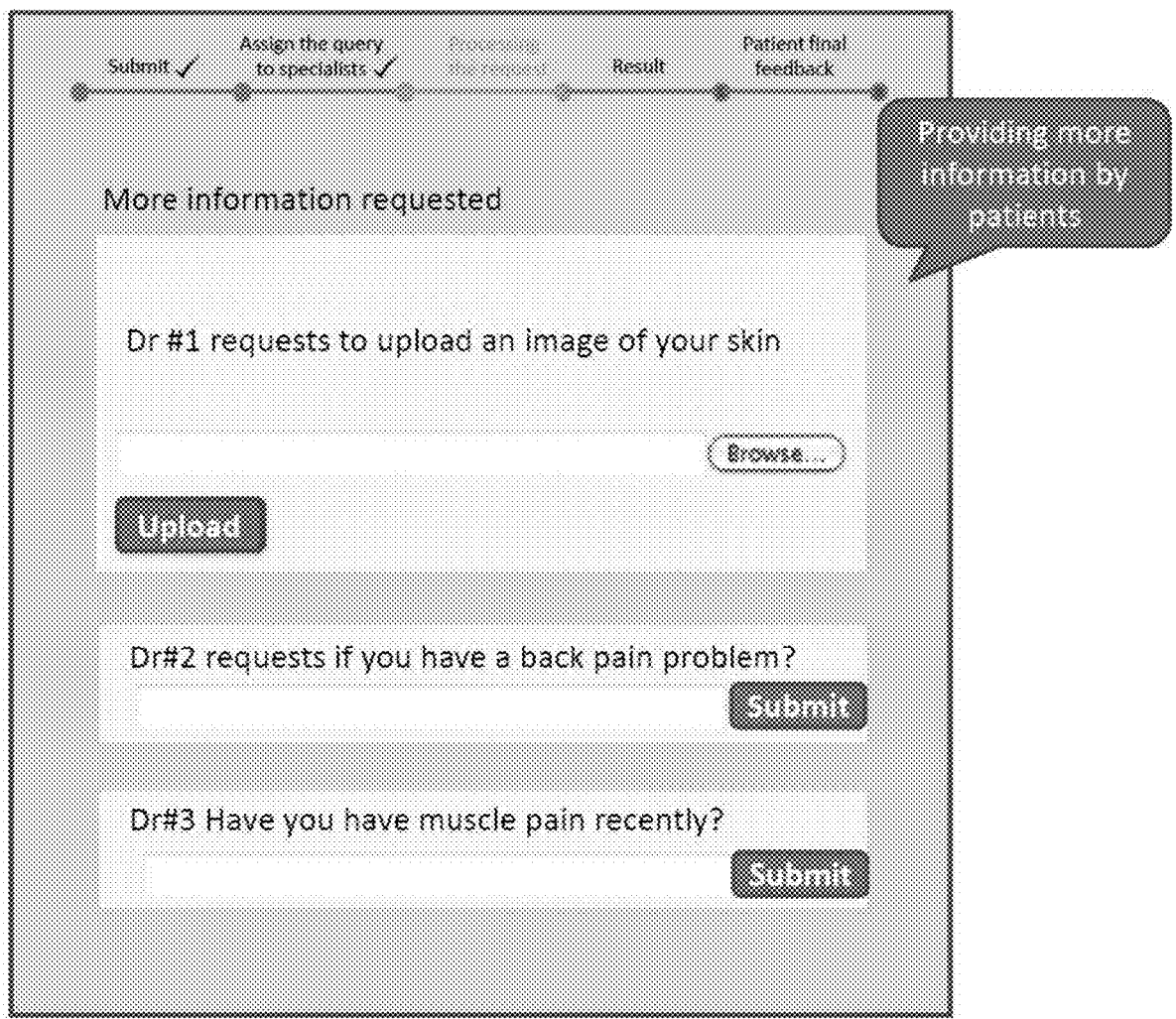
Figure 5D:
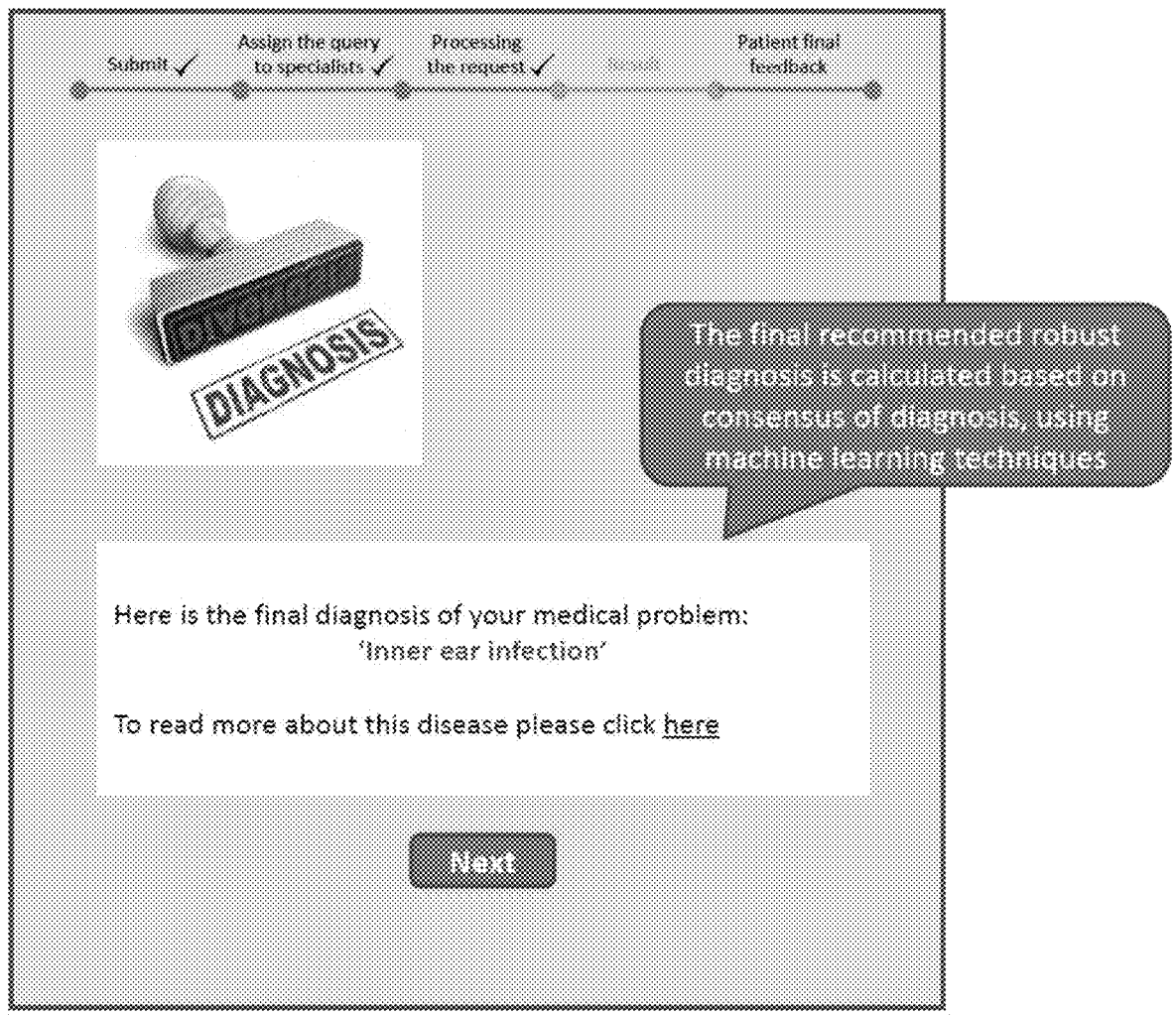
Figure 5E:
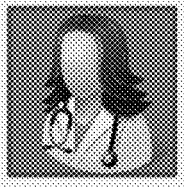

In some embodiments, a Graphical User Interface (GUI) may be utilized in conjunction with the method 100. As exemplary depicted in FIG. 5A-5E, the patient can interact with the graphical interface by inputting user symptoms 130 in FIG. 5A and the processed symptoms can trigger an interactive querying to the patient about the symptoms. In FIG. 5B, the user can be assigned to a team of doctors (e.g., step 102). As shown in FIG. 5B, the specialty classes of the physicians are identified and if the physician is a cognitive agent is identified. As shown in FIG. 5C, after the doctors have been assigned, the doctors may submit queries to the patients for more symptoms. As shown in FIG. 5D, a consensus diagnosis from all of the physicians (e.g., a top result of the list of diseases) may be presented to the user. In some embodiments (not shown), a list of diseases may be provided for the user. As shown in FIG. 5E, the user can provide feedback for each of the physicians and the cognitive agent based on their experience.

Thus, the present invention proposes a technical solution to the technical problem in the conventional techniques by intelligently providing physicians across a diverse number of specialties associated with the symptoms of the patient to reduce time and money spent on doctor visits to each particular physician.

For example, a patient may have had headache, dizziness and vertigo, and nausea for some days. She met a general practitioner (first specialty type) and the general practitioner's diagnosis was pregnancy. The patient the proceeded to spend the time and money to take a blood test and ultrasound, and she then met a women specialist for pregnancy (second specialty type) diagnosed that she was not pregnant. The general practitioner's second diagnosis was fatigue, which is the results of stress and pressure and she suggested the patient to stay home for a few days and have rest. However, the suggestion did not work for her, the symptoms got worse, and the patient had to spend two days in a hospital. Since her headache and dizziness were detected, the patient was suspicious for a brain problem, which was referred to a brain specialist and hthe patient took expensive medical tests, but it was not a brain problem. Lastly, she was suggested to visit an otolaryngologist (third specialty type) and the specialist recognized an inner ear infection.

That is, the present invention may provide a technical solution to the above exemplary technical problem of a patient required to spend time and money on multiple wrong diagnoses before finding a correct diagnoses. By at least the method 100, each of the diagnoses from the three specialty types of physicians may have been provided to the patient in a ranked list according to clustering her symptoms and extracting the specialty physicians and/or agent with which to consult.

Exemplary Aspects, Using a Cloud-Computing Environment

Although this detailed description includes an exemplary embodiment of the present invention in a cloud-computing environment, it is to be understood that implementation of the teachings recited herein are not limited to such a cloud-computing environment. Rather, embodiments of the present invention are capable of being implemented in conjunction with any other type of computing environment now known or later developed.

Cloud-computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client circuits through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud-computing environment is service oriented with a focus on statelessness, low coupling, modularity, and semantic interoperability. At the heart of cloud-computing is an infrastructure comprising a network of interconnected nodes.

Figure 6:
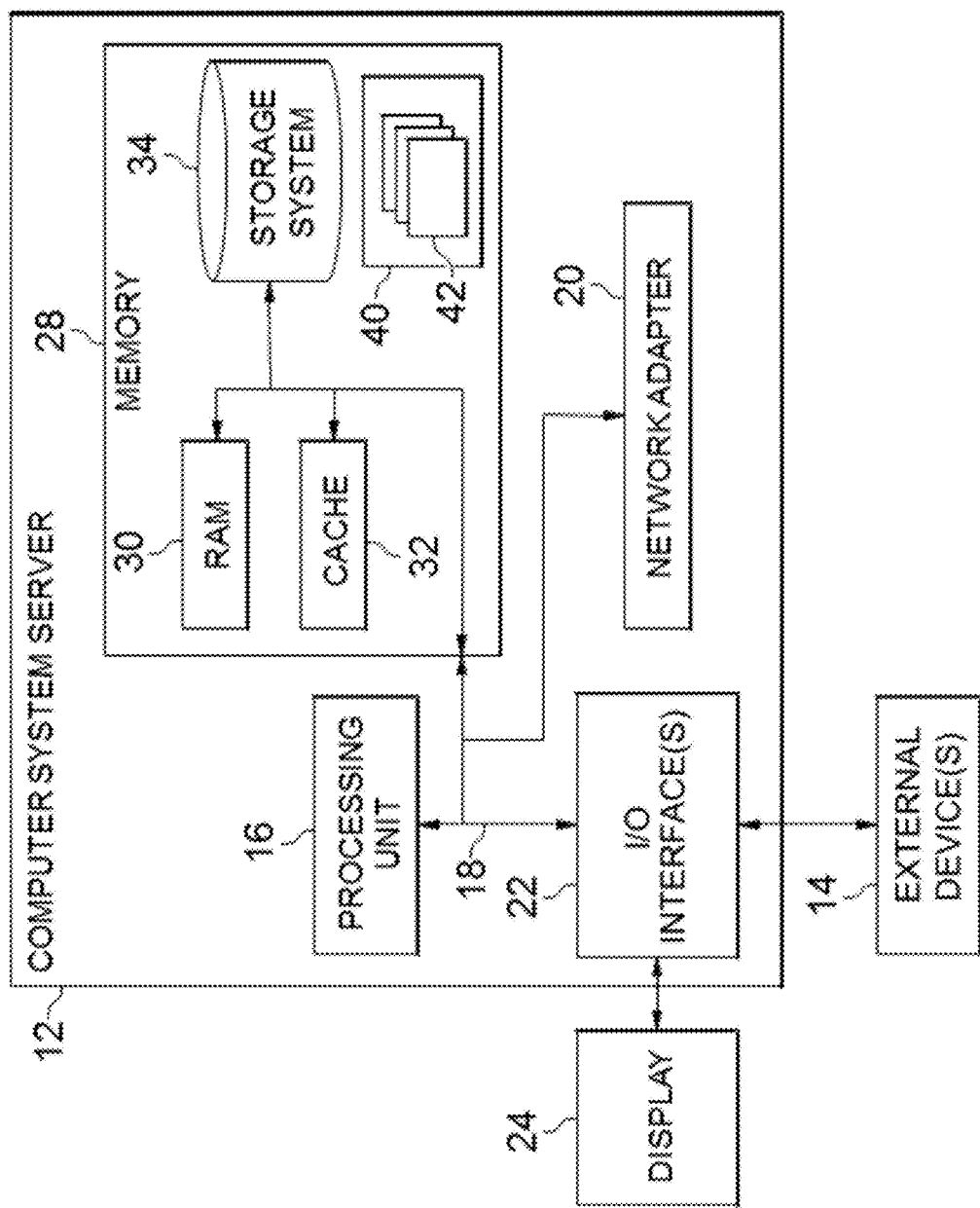
FIG. 6 depicts a cloud computing node 10 according to an embodiment of the present invention.

Referring now to FIG. 6, a schematic of an example of a cloud-computing node is shown. Cloud-computing node 10 is only one example of a suitable node and is not intended to suggest any limitation as to the scope of use or functionality of embodiments of the invention described herein. Regardless, cloud-computing node 10 is capable of being implemented and/or performing any of the functionality set forth herein.

Although cloud-computing node 10 is depicted as a computer system/server 12, it is understood to be operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop circuits, multiprocessor systems, microprocessor-based systems, set top boxes, programmable consumer electronics, network PCs, minicomputer systems, mainframe computer systems, and distributed cloud-computing environments that include any of the above systems or circuits, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud-computing environments where tasks are performed by remote processing circuits that are linked through a communications network. In a distributed cloud-computing environment, program modules may be located in both local and remote computer system storage media including memory storage circuits.

Referring again to FIG. 6, computer system/server 12 is shown in the form of a general-purpose computing circuit. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external circuits 14 such as a keyboard, a pointing circuit, a display 24, etc.; one or more circuits that enable a user to interact with computer system/server 12; and/or any circuits (e.g., network card, modem, etc.) that enable computer system/server 12 to communicate with one or more other computing circuits. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, circuit drivers, redundant processing units, external disk drive arrays, RAID systems, tape drives, and data archival storage systems, etc.

Figure 7:
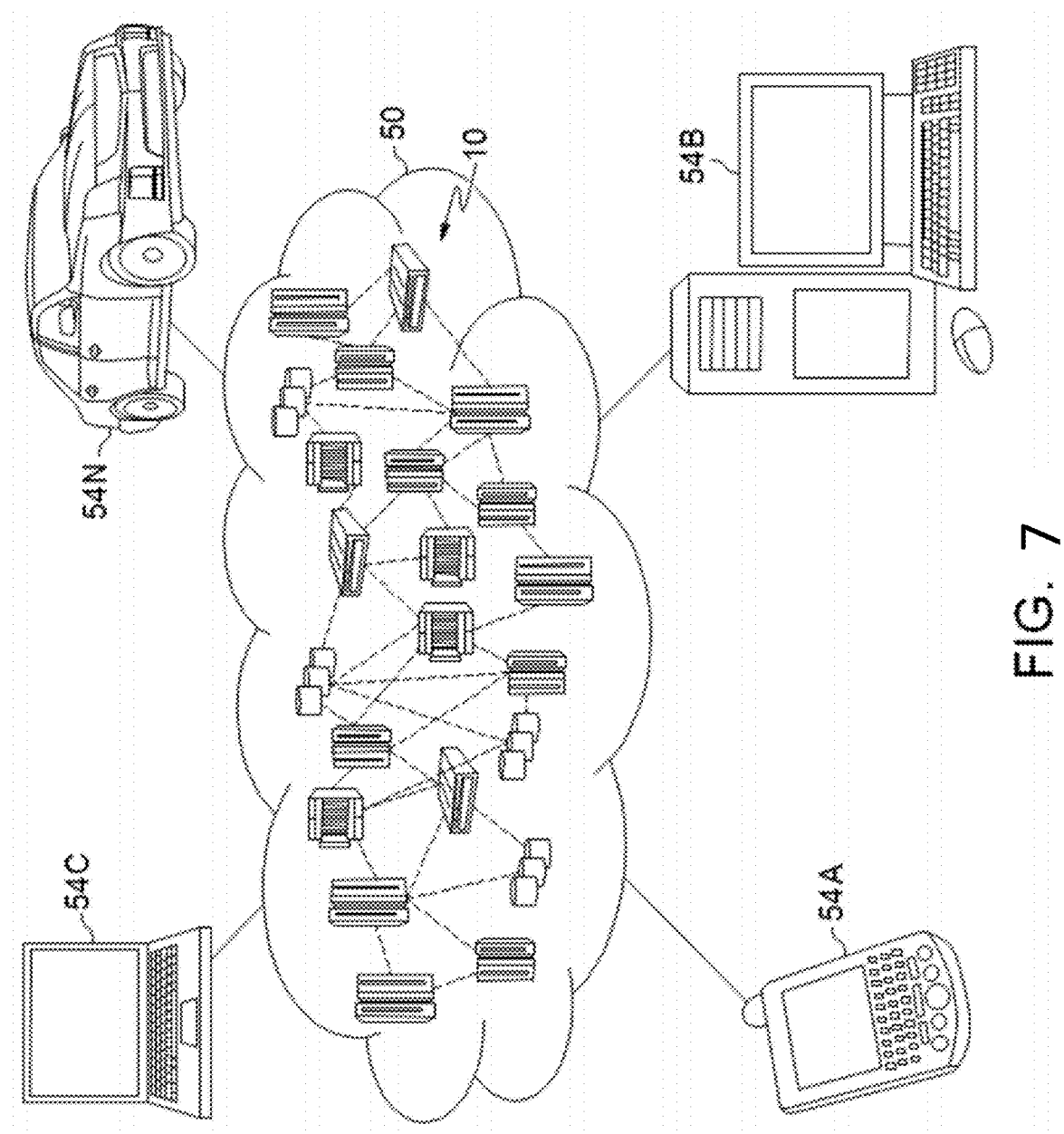
FIG. 7 depicts a cloud computing environment 50 according to an embodiment of the present invention.

Referring now to FIG. 7, illustrative cloud-computing environment 50 is depicted. As shown, cloud-computing environment 50 comprises one or more cloud-computing nodes 10 with which local computing circuits used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud-computing environment 50 to offer infrastructure, platforms and/or software as services for which a cloud consumer does not need to maintain resources on a local computing circuit. It is understood that the types of computing circuits 54A-N shown in FIG. 7 are intended to be illustrative only and that computing nodes 10 and cloud-computing environment 50 can communicate with any type of computerized circuit over any type of network and/or network addressable connection (e.g., using a web browser).

Figure 8:
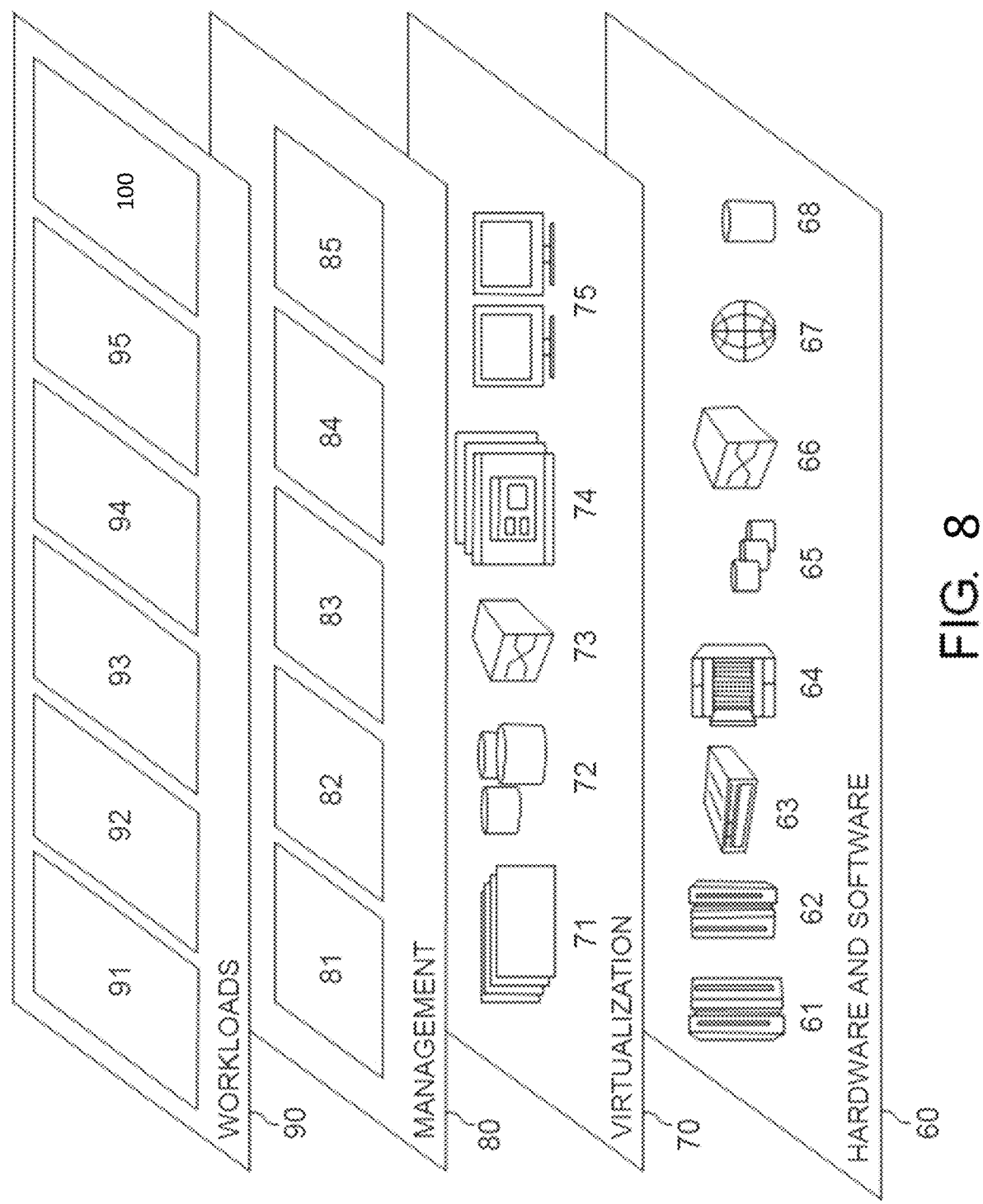
FIG. 8 depicts abstraction model layers according to an embodiment of the present invention.

Referring now to FIG. 8, an exemplary set of functional abstraction layers provided by cloud-computing environment 50 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage circuits 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud-computing environment. Metering and Pricing 82 provide cost tracking as resources are utilized within the cloud-computing environment, and billing or invoicing for consumption of these resources. In one example, these resources may comprise application software licenses. Security provides identity verification for cloud consumers and tasks, as well as protection for data and other resources. User portal 83 provides access to the cloud-computing environment for consumers and system administrators. Service level management 84 provides cloud-computing resource allocation and management such that required service levels are met. Service Level Agreement (SLA) planning and fulfillment 85 provide pre-arrangement for, and procurement of, cloud-computing resources for which a future requirement is anticipated in accordance with an SLA.

Workloads layer 90 provides examples of functionality for which the cloud-computing environment may be utilized. Examples of workloads and functions which may be provided from this layer include: mapping and navigation 91; software development and lifecycle management 92; virtual classroom education delivery 93; data analytics processing 94; transaction processing 95; and, more particularly relative to the present invention, the diagnosis method 100.

The present invention may be a system, a method, and/or a computer program product at any possible technical detail level of integration. The computer program product may include a computer-readable storage medium (or media) having computer-readable program instructions thereon for causing a processor to carry out aspects of the present invention.

The computer-readable storage medium can be a tangible device that can retain and store instructions for use by an instruction execution device. The computer-readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer-readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer-readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer-readable program instructions described herein can be downloaded to respective computing/processing devices from a computer-readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer-readable program instructions from the network and forwards the computer-readable program instructions for storage in a computer-readable storage medium within the respective computing/processing device.

Computer-readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer-readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer-readable program instructions by utilizing state information of the computer-readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer-readable program instructions.

These computer-readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer-readable program instructions may also be stored in a computer-readable storage medium that can direct a computer, a programmable data processing apparatus, and/or other devices to function in a particular manner, such that the computer-readable storage medium having instructions stored therein comprises an article of manufacture including instructions which implement aspects of the function/act specified in the flowchart and/or block diagram block or blocks.

The computer-readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

Further, Applicant's intent is to encompass the equivalents of all claim elements, and no amendment to any claim of the present application should be construed as a disclaimer of any interest in or right to an equivalent of any element or feature of the amended claim.

What is claimed is:

1. A computer-implemented diagnosis method that interacts with a cloud computing environment, the method comprising:

first:
  processing, via a cloud on-demand self-service running on an application on a graphical-user interface (GUI) that communicates with the cloud computing environment, a user input comprising medical symptoms expressed in nonprofessional terms,
  wherein, during the processing, the user input is converted from the nonprofessional terms from the user into medical terms based on running an expansion service to obtain the medical symptoms,
  wherein a relationship between the medical symptoms and a disease is determined using a first graph including a bipartite graph of disease to symptom relationships which indicates the relationship between symptoms and diseases,
  wherein each symptom is connected to one or more diseases and each disease is connected to one or more symptoms,
  wherein, the first graph maps the relationships between a single symptom and multiple different diseases,
  wherein a second graph is extracted from the first graph where nodes of the second graph represent the diseases of the first graph and the edges of the second graph represent the symptoms,
  wherein the second graph maps diseases with similar symptoms as strongly connected, whereas diseases that have different symptoms are loosely connected, thereby the nodes and edges are clustered in the second graph where each cluster represents a disease category corresponding to a type of specialty of a physician; and then, running a cognitive intelligent agent(s) based on machine learning classifiers determined from the first graph and the second graph:
  assigning, via the cloud computing environment, a user to a team of physicians and a cognitive agent that is run on the cloud computing environment, each of the physicians having a different medical specialty corresponding to the disease associated with the medical symptoms;
  producing, via the cloud computing environment, a consensus diagnosis from the team of physicians and the cognitive agent balancing different diagnosis by each of the team of physicians and the cognitive agent in order to determine the consensus diagnosis; and outputting, via the cloud computing environment to the cloud on-demand self-service running on the application on the graphical-user interface, multiple diseases that have one or more of the user input medical symptoms in common and the consensus diagnosis, wherein, during the processing of the user input running on the cloud on-demand self-service running on the application on the graphical-user interface, interactively querying the user on the graphical-user interface for additional information by using natural language processing running on the cloud environment to understand the user input and cause a search of medical databases for prior consensus diagnosis, wherein the multiple diseases that have one or more of the user input medical symptoms in common and the consensus diagnosis are displayed on the GUI such that the multiple diseases and each of the team of physicians including their credentials are displayed together on the GUI on a same screen in the application allowing the user to provide feedback, via the cloud on-demand self-service running on the application, for each of the physicians and the cognitive agent based on their experience while viewing each concurrently, further comprising, during the run phase, adjusting a physician accuracy score for each of the physicians on the team of physicians and the cognitive agent based on the feedback from the user entered into the application, the feedback from the user describing an accuracy of the consensus diagnosis.

2. The computer-implemented method of claim 1, wherein the assigning assigns the team of physicians based on a user preference for a category of the physicians comprising:
age;
gender; and
geo-location.

3. The computer-implemented diagnosis method of claim 1, wherein displaying the multiple diseases that have the one or more of the user input medical symptoms in common and the consensus diagnosis on the GUI is based on instructions received via the cloud on-demand self-service running on the application on the GUI communicates with the cloud computing environment, further comprising load-balancing between two or more clouds by using the cloud computing environment, the load-balancing uses a cloud computing model of a service delivery that includes two or more clouds of a private cloud, a community cloud, and a public cloud that remain unique entities but are bound together by technology that enables data and application portability that results in the load-balancing between the two or more clouds, and wherein the cloud computing environment handles generating the GUI.

4. A computer program product for diagnosis that interacts with a cloud computing environment, the computer program product comprising a computer-readable storage medium having program instructions embodied therewith, the program instructions executable by a computer to cause the computer to perform:
first:
processing, via a cloud on-demand self-service running on an application on a graphical-user interface (GUI) that communicates with the cloud computing environment, a user input comprising medical symptoms expressed in nonprofessional terms, wherein, during the processing, the user input is converted from the nonprofessional terms from the user into medical terms using based on running an expansion service to obtain the medical symptoms, wherein a relationship between the medical symptoms and a disease is determined using a first graph including a bipartite graph of disease to symptom relationships which indicates the relationship between symptoms and diseases, wherein each symptom is connected to one or more diseases and each disease is connected to one or more symptoms, wherein, the first graph maps the relationships between a single symptom and multiple different diseases, wherein a second graph is extracted from the first graph where nodes of the second graph represent the diseases of the first graph and the edges of the second graph represent the symptoms, wherein the second graph maps diseases with similar symptoms as strongly connected, whereas diseases that have different symptoms are loosely connected, thereby the nodes and edges are clustered in the second graph where each cluster represents a disease category corresponding to a type of specialty of a physician; and second, running a cognitive intelligent agent(s) based on machine learning classifiers determined from the first graph and the second graph:
assigning, via the cloud computing environment, a user to a team of physicians and a cognitive agent that is run on the cloud computing environment, each of the physicians having a different medical specialty corresponding to the disease associated with the medical symptoms;

producing, via the cloud computing environment, a consensus diagnosis from the team of physicians and the cognitive agent balancing different diagnosis by each of the team of physicians and the cognitive agent in order to determine the consensus diagnosis; and outputting, via the cloud computing environment to the cloud on-demand self-service running on the application on the graphical-user interface, multiple diseases that have one or more of the user input medical symptoms in common and the consensus diagnosis, wherein, during the processing of the user input running on the cloud on-demand self-service running on the application on the graphical-user interface, interactively querying the user on the graphical-user interface for additional information by using natural language processing running on the cloud environment to understand the user input and cause a search of medical databases for prior consensus diagnosis, wherein the multiple diseases that have one or more of the user input medical symptoms in common and the consensus diagnosis are displayed on the GUI such that the multiple diseases and each of the team of physicians including their credentials are displayed together on the GUI on a same screen in the application allowing the user to provide feedback, via the cloud on-demand self-service running on the application, for each of the physicians and the cognitive agent based on their experience while viewing each concurrently, further comprising, during the run phase, adjusting a physician accuracy score for each of the physicians on the team of physicians and the cognitive agent based on the feedback from the user entered into the application, the feedback from the user describing an accuracy of the consensus diagnosis.

5. The computer program product of claim 4, wherein the assigning assigns the team of physicians based on a user preference for a category of the physicians comprising:
age;
gender; and
geo-location.

6. The computer program product of claim 4, wherein displaying the multiple diseases that have the one or more of the user input medical symptoms in common and the consensus diagnosis on the GUI is based on instructions received via the cloud on-demand self-service running on the application on the GUI communicates with the cloud computing environment,
further comprising load-balancing between two or more clouds by using the cloud computing environment, the load-balancing uses a cloud computing model of a service delivery that includes two or more clouds of a private cloud, a community cloud, and a public cloud that remain unique entities but are bound together by technology that enables data and application portability that results in the load-balancing between the two or more clouds, and
wherein the cloud computing environment handles generating the GUI.

7. A diagnosis system that interacts with a cloud computing environment, said system comprising:
a processor; and
a memory, the memory storing instructions to cause the processor to perform:
first:
processing, via a cloud on-demand self-service running on an application on a graphical-user interface (GUI) that communicates with the cloud computing environment, a user input comprising medical symptoms expressed in nonprofessional terms,
wherein, during the processing, the user input is converted from the nonprofessional terms from the user into medical terms based on running an expansion service to obtain the medical symptoms,
wherein a relationship between the medical symptoms and a disease is determined using a first graph including a bipartite graph of disease to symptom relationships which indicates the relationship between symptoms and diseases,
wherein each symptom is connected to one or more diseases and each disease is connected to one or more symptoms,
wherein, the first graph maps the relationships between a single symptom and multiple different diseases,
wherein a second graph is extracted from the first graph where nodes of the second graph represent the diseases of the first graph and the edges of the second graph represent the symptoms,
wherein the second graph maps diseases with similar symptoms as strongly connected, whereas diseases that have different symptoms are loosely connected, thereby the nodes and edges are clustered in the second graph where each cluster represents a disease category corresponding to a type of specialty of a physician; and
second, running a cognitive intelligent agent(s) based on machine learning classifiers determined from the first graph and the second graph:
assigning, via the cloud computing environment, a user to a team of physicians and a cognitive agent that is run on the cloud computing environment, each of the physicians having a different medical specialty corresponding to the disease associated with the medical symptoms;
producing, via the cloud computing environment, a consensus diagnosis from the team of physicians and the cognitive agent balancing different diagnosis by each of the team of physicians and the cognitive agent in order to determine the consensus diagnosis; and
outputting, via the cloud computing environment to the cloud on-demand self-service running on the application on the graphical-user interface, multiple diseases that have one or more of the user input medical symptoms in common and the consensus diagnosis,
wherein, during the processing of the user input running on the cloud on-demand self-service running on the application on the graphical-user interface, interactively querying the user on the graphical-user interface for additional information by using natural language processing running on the cloud environment to understand the user input and cause a search of medical databases for prior consensus diagnosis,
wherein the multiple diseases that have one or more of the user input medical symptoms in common and the consensus diagnosis are displayed on the GUI such that the multiple diseases and each of the team of physicians including their credentials are displayed together on the GUI on a same screen in the application allowing the user to provide feedback, via the cloud on-demand self-service running on the application, for each of the physicians and the cognitive agent based on their experience while viewing each concurrently,
further comprising, during the run phase, adjusting a physician accuracy score for each of the physicians on the team of physicians and the cognitive agent based on the feedback from the user entered into the application, the feedback from the user describing an accuracy of the consensus diagnosis.

8. The diagnosis system of claim 7, wherein displaying the multiple diseases that have the one or more of the user input medical symptoms in common and the consensus diagnosis on the GUI is based on instructions received via the cloud on-demand self-service running on the application on the GUI communicates with the cloud computing environment,
further comprising load-balancing between two or more clouds by using the cloud computing environment, the load-balancing uses a cloud computing model of a service delivery that includes two or more clouds of a private cloud, a community cloud, and a public cloud that remain unique entities but are bound together by technology that enables data and application portability that results in the load-balancing between the two or more clouds, and
wherein the cloud computing environment handles generating the GUI.

\* \* \* \* \*